United States Patent
Redkar et al.

(10) Patent No.: US 7,001,886 B2
(45) Date of Patent: Feb. 21, 2006

(54) HOT MELT METHOD FOR PREPARING DIPHENHYDRAMINE TANNATE

(75) Inventors: Sham N. Redkar, Bound Brook, NJ (US); Raja G. Achari, Millington, NJ (US); James R. Schleck, Somerset, NJ (US); Vilas M. Chopdekar, Edison, NJ (US)

(73) Assignee: Jame Fine Chemicals, Inc., Bound Brook, NJ (US)

( * ) Notice: Subject to any disclaimer, the term of this patent is extended or adjusted under 35 U.S.C. 154(b) by 86 days.

(21) Appl. No.: 10/826,538

(22) Filed: Apr. 16, 2004

(65) Prior Publication Data

US 2004/0198667 A1    Oct. 7, 2004

Related U.S. Application Data

(63) Continuation-in-part of application No. 10/269,714, filed on Oct. 11, 2002, now abandoned, which is a continuation-in-part of application No. 10/017,131, filed on Dec. 14, 2001, now Pat. No. 6,677,381.

(51) Int. Cl.
*A61K 38/00*     (2006.01)
*C07H 13/02*     (2006.01)

(52) U.S. Cl. ......................................... 514/13; 536/119
(58) Field of Classification Search ................. 560/68; 424/464; 514/651, 649, 13; 536/119
See application file for complete search history.

(56) References Cited

U.S. PATENT DOCUMENTS

| 5,663,415 A | 9/1997 | Chopdekar et al. ........... 560/68 |
| 6,268,012 B1 * | 7/2001 | Sikora et al. ................ 426/640 |
| 6,287,597 B1 | 9/2001 | Gordziel ..................... 424/464 |
| 6,509,492 B1 | 1/2003 | Venkataraman .............. 560/68 |

* cited by examiner

*Primary Examiner*—Cecilia J. Tsang
*Assistant Examiner*—Taylor Victor Oh
(74) *Attorney, Agent, or Firm*—Jack Matalon

(57) ABSTRACT

The invention pertains to a method for preparing diphenhydramine tannate by reacting diphenhydramine free base at a temperature of about 75 to about 150° C. with tannic acid neat or as an aqueous slurry containing up to about 20 wt. % water. The diphenhydramine free base may be obtained by reacting a commercially available diphenhydramine salt such as diphenhydramine maleate with a base such as aqueous sodium hydroxide. The resultant diphenhydramine tannate has extended release properties and is useful in pharmaceutical compositions as an antihistamine for human beings.

11 Claims, No Drawings

HOT MELT METHOD FOR PREPARING DIPHENHYDRAMINE TANNATE

CROSS-REFERENCE TO RELATED APPLICATION

This application is a continuation-in-part of application Ser. No. 10/269,714 filed Oct. 11, 2002 now abandoned that in turn is a continuation-in-part of application Ser. No. 10/017,131 filed Dec. 14, 2001 now U.S. Pat. No. 6,677,381.

FIELD OF THE INVENTION

The invention pertains to a hot melt method for preparing diphenhydramine tannate.

BACKGROUND OF THE INVENTION

Diphenhydramine, i.e., 2-diphenylmethoxy-N,N-dimethylethanamine, is a well-known antihistamine. Since the compound is insoluble in water, it typically is administered in the form of its hydrochloride salt. Diphenhydramine hydrochloride has the molecular formula $C_{17}H_{21}NO \cdot HCl$, a molecular weight of 291.82, a melting point of 166–170° C. and a bitter taste. The hydrochloride is quite soluble in water (1 gram dissolves in 1 ml of water). It is typically administered to human beings in need of such medication in the form of tablets and/or suspensions. It frequently is administered as an antihistamine/antitussive composition consisting of diphenhydramine hydrochloride/dextromethorphan hydrobromide monohydrate.

The currently administered forms of diphenhydramine, i.e., generally an acid salt such as the hydrochloride, are disadvantageous in that they are absorbed very quickly in the mammalian body. Accordingly, although such forms provide prompt relief, multiple doses must be taken on a daily basis to provide an effective level of medicament over the prescribed period of treatment (generally several days to one week).

It would be very desirable if a form of diphenhydramine was available which would have extended-release properties, i.e., the diphenhydramine would be slowly released into the patient's bloodstream over a prolonged period of time. Until recently, the only slow-release forms of diphenhydramine that were available were those such as polymer-coated tablets. Such prior art formulations provided mixed results in that the diphenhydramine was not available for adsorption into the patient's bloodstream until the polymeric coating was dissolved, but thereafter the diphenhydramine was quickly absorbed and metabolized. The result is that frequently, the diphenhydramine had to again be administered to the patient within the period of only a few hours.

The foregoing problem was solved by converting the diphenhydramine free base into its tannate salt by reaction of the free base with tannic acid. The tannate salt stabilizes the diphenhydramine free base and, most importantly, imparts extended release properties to the diphenhydramine. In recent years, tannate salts of antihistamines have become known, e.g., see U.S. Pat. Nos. 5,599,846; 5,663,415; 6,037,358; 6,287,597; and 6,306,904.

Tannic acid is commercially available and is used in many industrial applications. It is frequently referred to as gallotannic acid, gallotannin; glycerite or tannin. It is a pale tan powder having a decomposition point of 210–215° C., and is highly soluble in water and alcohols. Its molecular formula is $C_{76}H_{52}O_{46}$; its CAS number is 1401-55-4. Tannic acid is typically produced from Turkish or Chinese nutgall and has a complex non-uniform chemistry and typically contains about 5–10 wt. % water.

Commercially available antihistamine tannate compositions are relatively impure. Such compositions are typically prepared by reacting the antihistamine free base with tannic acid in the presence of a volatile solvent, usually isopropanol. The yield is only fair (e.g. about 70%) and decomposition products e.g. 2–5 wt. %, and a significant amount of the volatile solvent, e.g. 6–10 wt. %, based on the weight of the composition, remains with the product and cannot be removed.

Typically, in the conventional isopropanol route, the antihistamine free base and the tannic acid will be present in the isopropanol at a concentration of about 20 wt. %, based on the weight of the reaction mixture. The reaction mixture is stirred for about one hour, while maintaining a temperature of 60–70° C. The reaction mixture is cooled to room temperature and filtered. The precipitate is vacuum dried for an extended period of time at a temperature of 60–80° C. A yield of product of only about 70% is obtained and the product purity will be about 85–90 wt. %, based on the weight of the composition (the impurities consist of isopropanol and decomposition products which cannot be removed).

Many antihistamine tannates are heat sensitive and therefore undergo decomposition quite readily upon prolonged exposures to temperatures as low as 50° C. Accordingly, even when the solvent utilized in its preparation has a relatively high vapor pressure such as is in the case of isopropanol, it is impossible to reduce the solvent content below about 6 wt. %, based on the weight of the antihistamine tannate composition, even at reduced pressures and very mild elevated temperatures. Moreover, from an environmental point, it would be most desirable if the antihistamine tannate could be prepared such that the use of volatile solvents could be avoided.

The process disclosed in U.S. Pat. No. 5,663,415 represents a significant improvement over the isopropanol route. The process disclosed in the '415 patent involves three steps:

(a) the antihistamine in the form of its free base is contacted with tannic acid in the presence of water at a maximum temperature which will not cause decomposition of the antihistamine tannate to an extent of greater than about 5 wt %, based on the weight of the antihistamine tannate;

(b) the antihistamine is allowed to remain in contact with the tannic acid in the presence of water for a period of time of about 5 minutes to 4 hours at said maximum temperature; and (c) the antihistamine tannate resulting from step (b) is freeze-dried at a temperature and at a reduced pressure and for such period of time that (i) at least about 90 wt. % of the water is removed from the antihistamine tannate and (ii) decomposition of the antihistamine tannate will be limited to a maximum of about 5 wt. %.

The '415 patent discloses a three-step method that results in the production of pure antihistamine tannate compositions having a minimum purity level of at least 90 wt. %, usually at least 95 wt. % and often at least 98 wt. %, based on the weight of the composition, with a yield of at least about 90% and often with a yield in excess of 97%. The chief "impurity" present in the compositions prepared by the process of the '415 patent is water which is present in an amount of 1–5 wt. %, based on the weight of the composition.

Although the process disclosed in the '415 patent represents a dramatic improvement leading to very pure antihistamine tannate compositions, it has several drawbacks: freeze-drying is quite time-consuming (typically 30–36 hours to remove 1 liter of water) and expensive and requires specialized equipment in order to achieve the reduced pressures and temperature required to dry the antihistamine tannate composition, i.e., a pressure of not greater than about 500 milliTorr and a temperature in the range of about −60° C. to −20° C. Such specialized equipment also limits the amount of product that can be processed within a reasonable amount of time.

DETAILED DESCRIPTION OF THE INVENTION

In accordance with the process of the invention, diphenhydramine tannate is prepared by reacting diphenhydramine free base with tannic acid. If the diphenhydramine is present in the form of a salt (typically a maleate), the salt is neutralized with a stoichiometric amount of a base such as aqueous sodium or potassium hydroxide (e.g., 10 wt. % concentration) and the resulting diphenhydramine free base layer is washed free of salts.

The diphenhydramine free base is heated to a temperature of about 75 to about 150° C., preferably 80 to 130° C., and tannic acid is slowly added, while mixing, to the diphenhydramine free base over a period of a few minutes to about one hour. The reaction mixture is continuously stirred while maintaining such temperature for a period of about 10 minutes to about 2 hours. Thereafter, the reaction mixture is cooled to room temperature.

If the process is carried out with the tannic acid utilized neat, the resultant diphenhydramine tannate need not be dried (it will, however, contain 1–3 weight percent of water since the tannic acid as commercially available contains 5–10 wt. % water). The resultant diphenhydramine tannate is preferably milled to form a free-flowing powder preferably to a particle size of about 50 to about 200 mesh.

The tannic acid maybe utilized neat, i.e., no additional diluent or solvent is employed during the reaction. However, a small amount of water, e.g. 5–20 wt. %, may be added to facilitate the stirring of the reaction mass that is quite viscous. The product will be quite pure, i.e., it will have a purity level above 95 wt. %, preferably above 97 wt. % and most preferably 99 wt. % or greater, excluding any water which may be present. Since the product is intended to be ingested, a water content of up to 15 wt. % is immaterial. If desired, the water content of the product may be reduced in a separate step by well-known processes, e.g. drying under vacuum (about 1 mm Hg) at about 65 to about 75° C. for 1–10 hours or more, sparging with nitrogen for 1 to 10 hours or more, etc.

The molar ratio of the diphenhydramine free base to the tannic acid is generally in the range of about 4 to about 8, preferably 5 to 6, moles of diphenhydramine free base per mole of tannic acid.

The diphenhydramine tannate prepared by the hot melt method of the invention has the following physical properties: It has a softening point in the range as follows (moisture content is determined by K. F. analysis):

| Softening Point, ° C. | Moisture Content, % |
|---|---|
| 45–50 | 12.25 |
| 65–70 | 6.4 |
| 70–75 | 4.1 |
| 100–105 | 1.47 |

The diphenhydramine tannate of the invention may be prepared for oral administration in the form of pharmaceutically acceptable compositions such as powders, capsules, elixirs, syrups, etc. Preferably, the compositions are prepared in the form of tablets containing about 5 to about 50 mg of diphenhydramine tannate per tablet or as a suspension, i.e., a liquid, wherein each 5 ml (teaspoon) of liquid would contain about 2.5 to about 30 mg of the diphenhydramine tannate.

Tablets containing the unique diphenhydramine tannate of the invention may be prepared in a conventional manner by the addition of suitable pharmaceutical carriers, including fillers, diluents, lubricants and the like as well as conventional and well known binding and disintegrating agents. A typical tablet composition of the present invention will contain, in addition to the diphenhydramine tannate, microcrystalline cellulose, corn starch, magnesium stearate, croscarmellose sodium and coloring matter.

The suspension formulations of the diphenhydramine tannate of the present invention will typically additionally contain citric acid, caramel, glycerin, sorbitol solution, propylene glycol, saccharin sodium, sodium benzoate, flavoring agent and purified water.

If desired, the diphenhydramine tannate composition of the invention may be formulated with other pharmaceutically active ingredients such as expectorants, antihistamines and antitussives, e.g., dextromethorphan, chlorpheniramine brompheniramine, dextrochlorpheniramine, dextrobrompheniramine, pyrilamine, phenylephrine, ephedrine, pseudoephedrine, carbetapentane, carbinoxamine, guaifenesin, and the like. Typically, these other active ingredients may be employed in the form of their free bases or as their salts, e.g., citrates, maleates, hydrobromides, hydrochlorides, tannates, etc. Of course, the dosage of the diphenhydramine tannate of the present invention, alone or in combination with other pharmaceutically active ingredients to be administered, will be dependent on the age, health and weight of the recipient, types of concurrent treatment, if any, frequency of treatment and effect desired.

The following nonlimting examples shall serve to illustrate the present invention. Unless otherwise indicated, all parts and percentages are on a weight basis.

EXAMPLE 1

Preparation of Diphenhydramine Free Base

A 500 ml round bottom flask equipped with a stirrer, thermometer and heating mantle was set up. The flask was charged with 176 g of a 10% aqueous sodium hydroxide solution. Thereafter, 118 g (0.40 mole) diphenhydramine hydrochloride was slowly added, with stirring, to the flask at room temperature. The reaction mixture was then stirred for 30 minutes at 45–50° C. The reaction mixture was allowed to settle for 15 minutes and the organic layer was separated (the pH of the layer was 12.8). The organic layer consisting of the diphenhydramine free base was washed by mixing it with 100 ml of purified water and maintaining a temperature of 70–75° C. for one hour, while stirring. Stirring was then discontinued and the phases were allowed to split over a period of one hour. The lower organic layer consisting of the diphenhydramine free base was then separated. The yield of the free base was found to be 104 g (about 99% of theory) and it had a moisture content of 2.18% as determined by Karl. Fischer (K. F.) analysis.

EXAMPLE 2

Conversion of Diphenhydramine Free Base to Diphenhydramine Tannate

A 250 ml beaker, stainless steel hot water bath, stirrer and thermometer were set up. The hot water bath containing the beaker was heated to 75–80° C. and 8 g of purified water were charged to the beaker (the small amount of water was used to facilitate stirring). 25 g (0.1 mole) of the diphenhydramine free base prepared in accordance with Example 1 were charged to the beaker and stirring was initiated for five minutes. Thereafter, 34 g (0.02 mole) of tannic acid having a moisture content of 4% (as determined by K. F. analysis) was charged, in small increments, over a period of 30 minutes, while maintaining stirring and an external temperature of 75 to 80° C. (the molar ratio of diphenhydramine free base to tannic acid was 5:1). The reaction mixture consisting of a thick slurry was stirred for one hour while maintaining an external temperature of 75 to 80° C. The reaction product was then removed from the beaker and placed in a dish to cool and solidify over a period of 1 hour. The resultant diphenhydramine tannate product was pulverized and dried in air. The moisture content was of the product was 1.47% by K. F. analysis.

The following test was employed to determine the completeness of the reaction between the diphenhydramine free base and the tannic acid: 2 g of the pulverized diphenhydramine tannate product were mixed with 110 g of methylene chloride for 10 minutes using a magnetic stirrer. Thereafter, the reaction mixture was filtered through a fluted filter paper and the residue remaining on the filter paper was dried under a heat lamp for about 1 hour. The methylene chloride filtrate was evaporated to dryness, leaving behind a residue of 0.008 g corresponding to 0.4 wt. %. Thus, the percentage of completion of the reaction was 99.6%.

The base assay of the diphenyhydramine tannate was found to be 42.8% as determined by conventional titration using an acetic acid solution of perchloric acid and crystal violet as the indicator. The theoretical base assay is 42.9%. Thus, the diphenhydramine tannate had a purity level of 99.8%.

What is claimed is:

1. A hot melt method for preparing diphenhydramine tannate which comprises reacting diphenhydramine free base with tannic acid in the presence of 0 to about 20 wt. % water at a temperature of about 80 to about 150° C. and thereafter recovering the resultant diphenhydramine tannate.

2. The method of claim 1 wherein the reaction is carried out at a temperature of 80 to 100° C.

3. The method of claim 1 wherein the diphenhydramine free base is employed in an amount of about 4 to about 8 moles of the free base per mole of tannic acid.

4. The method of claim 3 wherein the diphenhydramine free base is employed in an amount of 5 to 6 moles of the free base per mole of tannic acid.

5. The method of claim 1 wherein the recovered diphenhydramine tannate is subsequently dried under vacuum at a temperature of about 65 to about 75° C. for a period of 1 to 10 hours or more.

6. The method of claim 1 wherein the resultant diphenhydramine tannate is dried by sparging with nitrogen for a period of 1 to 10 hours or more.

7. The method of claim 1 wherein the resultant diphenhydramine tannate is milled to provide a free-flowing powder.

8. The method of claim 8 wherein the powder has a particle size in the range of about 50 to about 200 mesh.

9. The method of claim 1 wherein the diphenhydramine free base is obtained by reacting a diphenhydramine salt with the stoichiometric amount of a base.

10. The method of claim 10 wherein the diphenhydramine salt consists of diphenhydramine maleate.

11. The method of claim 10 wherein the base consists of aqueous sodium hydroxide.

* * * * *